US010420883B2

United States Patent
Diianni et al.

(10) Patent No.: US 10,420,883 B2
(45) Date of Patent: Sep. 24, 2019

(54) FLUID DELIVERY DEVICE, TRANSCUTANEOUS ACCESS TOOL AND FLUID DRIVE MECHANISM FOR USE THEREWITH

(71) Applicant: Insulet Corporation, Billerica, MA (US)

(72) Inventors: Steven Diianni, Danvers, MA (US); Ian McLaughlin, Boxborough, MA (US); Jason Brian O'Connor, South Boston, MA (US); Robert Campbell, Waltham, MA (US); Kevin Schmid, Boxford, MA (US)

(73) Assignee: Insulet Corporation, Bedford, MA (US)

( * ) Notice: Subject to any disclaimer, the term of this patent is extended or adjusted under 35 U.S.C. 154(b) by 643 days.

(21) Appl. No.: 15/226,510

(22) Filed: Aug. 2, 2016

(65) Prior Publication Data

US 2017/0128664 A1    May 11, 2017

Related U.S. Application Data

(63) Continuation of application No. 13/854,456, filed on Apr. 1, 2013, now Pat. No. 9,402,950, which is a
(Continued)

(51) Int. Cl.
*A61M 5/145* (2006.01)
*A61B 5/145* (2006.01)
(Continued)

(52) U.S. Cl.
CPC ..... *A61M 5/14566* (2013.01); *A61B 5/14532* (2013.01); *A61B 5/14865* (2013.01);
(Continued)

(58) Field of Classification Search
CPC ............ A61M 5/1452; A61M 5/14248; A61M 5/14244; A61M 5/14566;
(Continued)

(56) References Cited

U.S. PATENT DOCUMENTS

| 5,261,884 A | 11/1993 | Stern et al. |
| 5,503,628 A | 4/1996 | Fetters et al. |

(Continued)

FOREIGN PATENT DOCUMENTS

| EP | 2397181 A1 | 12/2011 |
| EP | 2830499 | 10/2013 |

(Continued)

OTHER PUBLICATIONS

EPO Search Report dated Nov. 11, 2015, received in corresponding Application No. 13768938.6, 7 pgs.
(Continued)

*Primary Examiner* — Imani N Hayman
*Assistant Examiner* — Tiffany Legette
(74) *Attorney, Agent, or Firm* — Grossman Tucker Perreault & Pfleger PLLC

(57) ABSTRACT

A fluid delivery device comprising a fluid reservoir; a transcutaneous access tool fluidly coupled to the fluid reservoir; and a drive mechanism for driving fluid from the reservoir, the drive mechanism comprising a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through when disengaged and is configured to grip the nut when engaged such that the drive wheel rotates the nut to advance the drive rod and the plunger into the reservoir.

15 Claims, 6 Drawing Sheets

Related U.S. Application Data continuation of application No. PCT/US2013/034674, filed on Mar. 29, 2013.

(60) Provisional application No. 61/618,028, filed on Mar. 30, 2012.

(51) Int. Cl.

| | |
|---|---|
| *A61B 5/1486* | (2006.01) |
| *F04B 9/02* | (2006.01) |
| *A61M 5/142* | (2006.01) |
| *A61M 5/172* | (2006.01) |
| *A61M 5/158* | (2006.01) |
| *A61M 5/32* | (2006.01) |
| *A61M 5/14* | (2006.01) |

(52) U.S. Cl.
CPC ...... *A61M 5/1452* (2013.01); *A61M 5/14244* (2013.01); *A61M 5/14248* (2013.01); *A61M 5/158* (2013.01); *A61M 5/1723* (2013.01); *F04B 9/02* (2013.01); *A61M 5/3291* (2013.01); *A61M 2005/1403* (2013.01); *A61M 2005/14252* (2013.01); *A61M 2005/14506* (2013.01); *A61M 2230/201* (2013.01); *F04C 2270/041* (2013.01)

(58) Field of Classification Search
CPC ........... A61M 2005/1403; A61M 2005/14252; A61M 2005/14506; A61B 5/14532; A61B 5/14865

See application file for complete search history.

(56) References Cited

U.S. PATENT DOCUMENTS

| | | | |
|---|---|---|---|
| 7,018,360 | B2 | 3/2006 | Flaherty et al. |
| 7,128,727 | B2 | 10/2006 | Flaherty et al. |
| 7,144,384 | B2 | 12/2006 | Gorman |
| 9,402,950 | B2 | 8/2016 | DiIanni et al. |
| 2002/0032374 | A1 | 3/2002 | Holker et al. |
| 2003/0163097 | A1 | 8/2003 | Fleury et al. |
| 2004/0010207 | A1 | 1/2004 | Flaherty et al. |
| 2004/0064088 | A1* | 4/2004 | Gorman ............ A61M 5/14276 604/93.01 |
| 2004/0092865 | A1 | 5/2004 | Flaherty et al. |
| 2005/0020980 | A1 | 1/2005 | Inoue et al. |
| 2005/0203461 | A1 | 9/2005 | Flaherty et al. |
| 2005/0238507 | A1* | 10/2005 | DiIanni ............. A61M 5/14244 417/415 |
| 2006/0155210 | A1 | 7/2006 | Beckman et al. |
| 2006/0178633 | A1 | 8/2006 | Garibotto et al. |
| 2006/0253085 | A1 | 11/2006 | Geismar et al. |
| 2006/0282290 | A1 | 12/2006 | Flaherty et al. |
| 2007/0005018 | A1 | 1/2007 | Tekbuchava |
| 2007/0118405 | A1 | 5/2007 | Campbell et al. |
| 2007/0282269 | A1 | 12/2007 | Carter et al. |
| 2008/0004515 | A1 | 1/2008 | Jennewine |
| 2008/0051738 | A1 | 2/2008 | Griffin |
| 2009/0062767 | A1 | 3/2009 | Van Antwerp et al. |
| 2009/0198215 | A1 | 8/2009 | Chong et al. |
| 2010/0152658 | A1 | 6/2010 | Hanson et al. |
| 2011/0054399 | A1 | 3/2011 | Chong et al. |
| 2011/0230833 | A1 | 9/2011 | Landman et al. |
| 2012/0078161 | A1 | 3/2012 | Masterson et al. |
| 2014/0127048 | A1 | 5/2014 | DiIanni et al. |
| 2014/0128839 | A1 | 5/2014 | DiIanni et al. |
| 2014/0142508 | A1 | 5/2014 | DiIanni et al. |

FOREIGN PATENT DOCUMENTS

| | | |
|---|---|---|
| WO | 9856293 A1 | 12/1998 |
| WO | 2008133702 A1 | 11/2008 |
| WO | 2013149186 | 10/2013 |

OTHER PUBLICATIONS

PCT International Search Report and Written Opinion dated Aug. 6, 2013, received in corresponding PCT Application No. PCT/US13/34674, pp. 1-19.
International Preliminary Report on Patentability dated Oct. 9, 2014, issued in PCT Patent Application No. PCT/US2013/034674, 15 pages.
U.S. Office Action dated Mar. 31, 2015, issued in U.S. Appl. No. 13/854,456, 11 pages.
U.S. Office Action dated Aug. 4, 2015, issued in U.S. Appl. No. 13/854,463 11 pages.
U.S. Office Action dated Sep. 23, 2015, issued in U.S. Appl. No. 13/854,456, 13 pages.
Notice of Allowance dated Mar. 25, 2016, issued in U.S. Appl. No. 13/854,456, 9 pages.
U.S. Office Action dated May 17, 2016, issued in U.S. Appl. No. 13/854,445, 11 pages.
U.S. Office Action dated May 31, 2016, issued in U.S. Appl. No. 13/854,463, 16 pages.
U.S. Office Action dated Jan. 25, 2017, issued in U.S. Appl. No. 13/854,445, 23 pages.
U.S. Office Action dated Mar. 3, 2017, issued in U.S. Appl. No. 13/854,463, 12 pages.
U.S. Office Action dated Oct. 31, 2017, issued in U.S. Appl. No. 13/854,445, 15 pages.
U.S. Office Action dated Oct. 31, 2017, issued in U.S. Appl. No. 13/854,463 13 pages.
Notice of Allowance dated May 21, 2018, issued in U.S. Appl. No. 13/854,463, 7 pages.
Notice of Allowance dated May 23, 2018, issued in U.S. Appl. No. 13/854,445, 8 pages.

* cited by examiner

FLUID DELIVERY DEVICE, TRANSCUTANEOUS ACCESS TOOL AND FLUID DRIVE MECHANISM FOR USE THEREWITH

CROSS-REFERENCE TO RELATED APPLICATIONS

This application is a continuation of U.S. patent application Ser. No. 13/854,456 filed Apr. 1, 2013, which is a continuation of PCT Application Serial No. PCT/US13/34674 filed Mar. 29, 2013 and claims the benefit of the filing date of U.S. Provisional Application Ser. No. 61/618,028, filed Mar. 30, 2012, the teachings of which are incorporated herein by reference.

TECHNICAL FIELD

The present invention relates to fluid delivery devices for delivering therapeutic liquids to a patient, and more particularly, to an infusion pump for delivering therapeutic liquids to a patient.

BACKGROUND INFORMATION

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump, to improve the comfort to the user, and/or to incorporate continuous glucose monitoring (CGM). These pumps also include fluid driving mechanisms for driving fluid from a reservoir through the transcutaneous access tool. The fluid driving mechanisms may also be improved to facilitate assembly and use of the pump.

SUMMARY

The present disclosure provides various fluid delivery devices to deliver a liquid medicine or other therapeutic fluid to a patient subcutaneously. In certain embodiments the fluid delivery device may comprise an ambulatory insulin infusion device to administer insulin to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, the drive mechanism may comprise a clutch mechanism. As explained herein, by using a clutch mechanism, the number of fluid path prime pulses to prime the pump may be reduced and a full and proper priming of the fluid path before placement on the body may be better assured. The clutch mechanism may also be made suitable for other drug applications without significant redesign, and be more easily inspected than conventional drive mechanisms for infusion devices.

In certain embodiments, the fluid delivery device may comprise a fluid reservoir; a transcutaneous access tool fluidly coupled to the fluid reservoir; and a drive mechanism for driving fluid from the reservoir. The drive mechanism may comprise a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through the clutch mechanism when disengaged and is configured to grip the nut when engaged such that the drive wheel rotates the nut to advance the leadscrew and the plunger into the reservoir.

In certain embodiments, the fluid delivery device may comprise a fluid reservoir; a transcutaneous access tool fluidly coupled to the fluid reservoir; and a drive mechanism for driving fluid from the reservoir. The drive mechanism may comprise a plunger received in the reservoir; an elongated assembly comprising a first elongated member and a second elongated member; the first elongated member extending from the plunger; the second elongated member coupled to the first elongated member; a drive wheel; and a clutch mechanism coupled to the drive wheel, wherein the clutch mechanism is configured to allow the second elongated member to pass through when disengaged and is configured to grip the second elongated member when engaged such that the drive wheel rotates the second elongated member to advance the first elongated member and the plunger into the reservoir.

In certain embodiments, a method of operating a foregoing fluid delivery device may comprise providing the fluid delivery device; holding the clutch mechanism in a disengaged position; filling the fluid reservoir with fluid; passing the second elongated member through the clutch mechanism such that the plunger is retracted within the reservoir; releasing the clutch mechanism from the disengaged position; and engaging the clutch mechanism with the second elongated member.

BRIEF DESCRIPTION OF THE DRAWINGS

These and other features and advantages will be better understood by reading the following detailed description, taken together with the drawings wherein.

DETAILED DESCRIPTION

Figure 1:
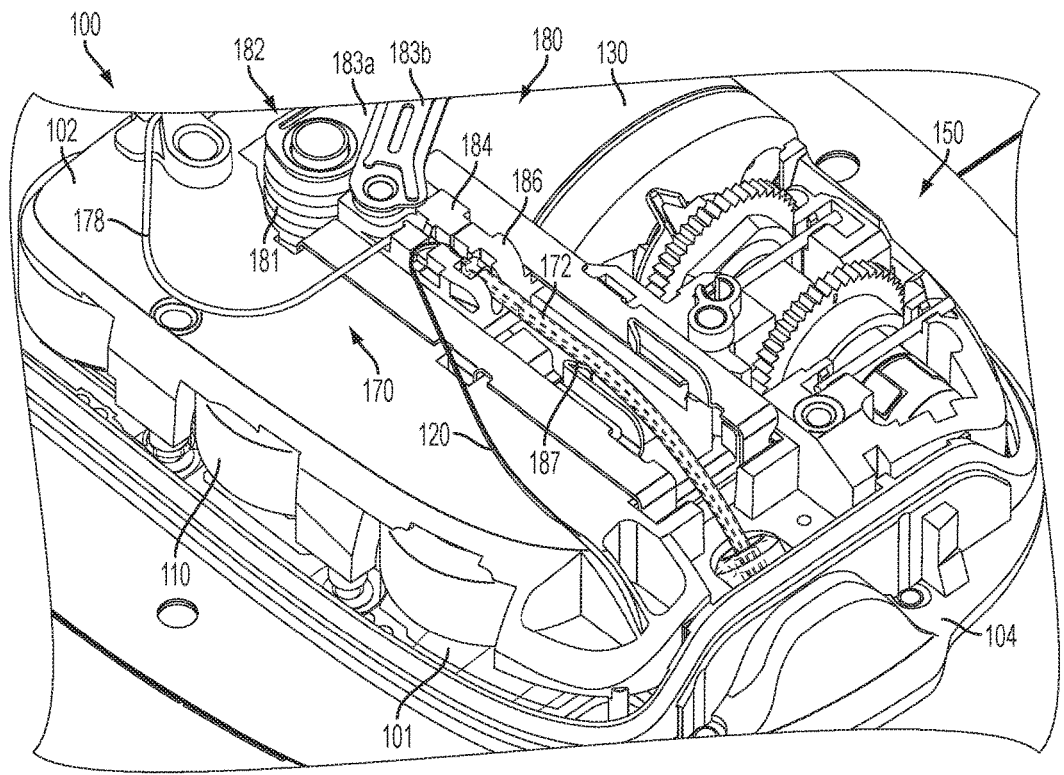
FIG. 1 is a top perspective view of a fluid delivery device with a transcutaneous access tool insertion mechanism in a pre-deployment position, consistent with the present disclosure.
Figure 2:
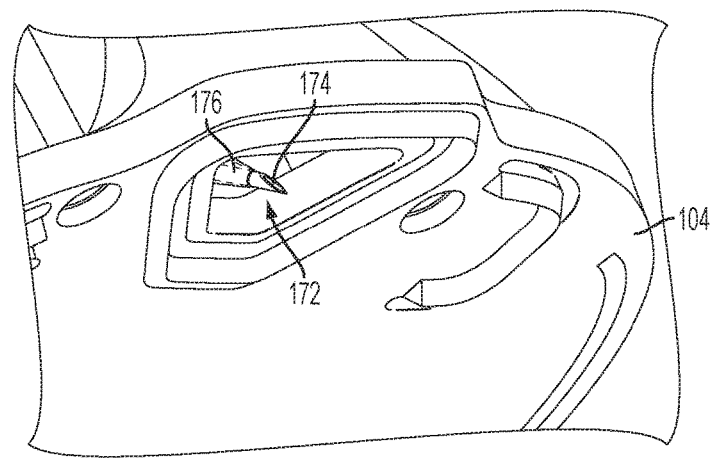
FIG. 2 is a bottom perspective view of a needle and cannula retracted into the fluid delivery device in the pre-deployment position shown in FIG. 1.
Figure 3:
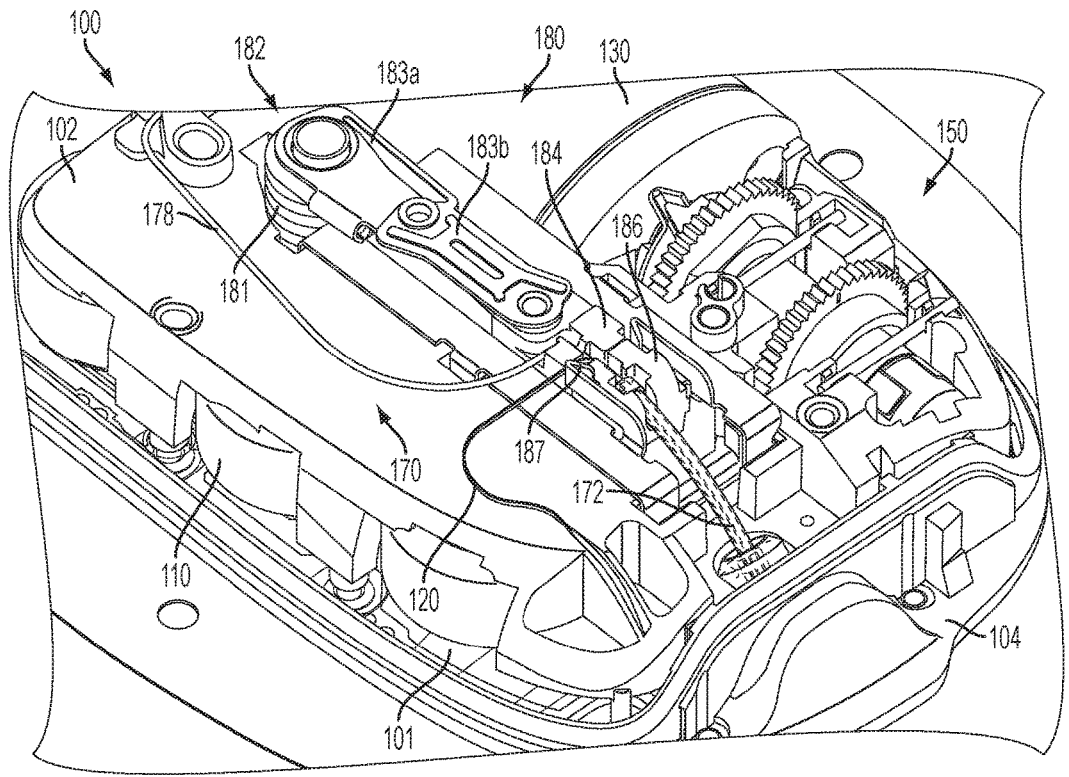
FIG. 3 is a top perspective view of the fluid delivery device shown in FIG. 1 with the insertion mechanism in an intermediate position.
Figure 4:
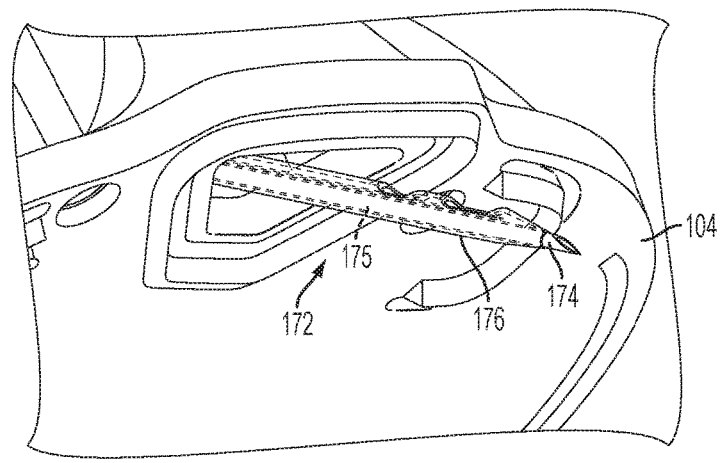
FIG. 4 is a bottom perspective view of the needle and cannula extending from the fluid delivery device in the intermediate position shown in FIG. 3.
Figure 5:
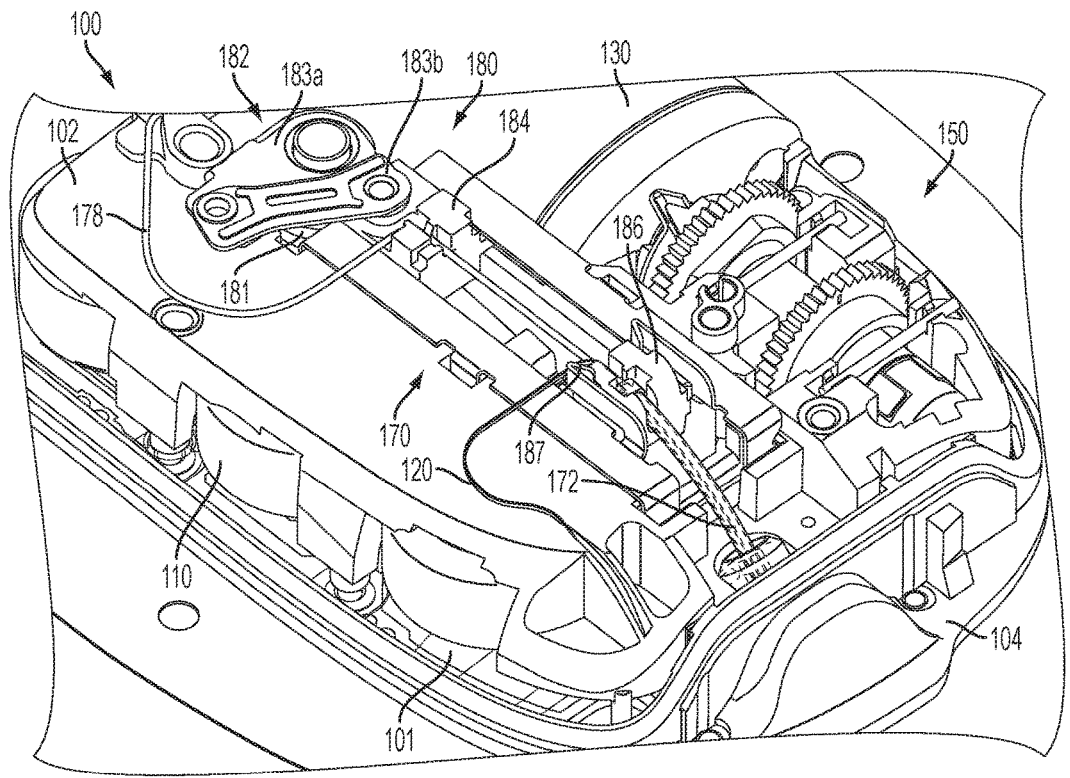
FIG. 5 is a top perspective view of the fluid delivery device shown in FIG. 1 with the insertion mechanism in a post-deployment position.

A fluid delivery device, consistent with embodiments of the present disclosure, may be used to deliver a therapeutic fluid (e.g. a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory insulin infusion device.

In other embodiments, a fluid delivery device may be used to deliver a therapeutic fluid to a patient with integrated monitoring, such as continuous glucose monitoring (CGM). In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine (e.g. insulin), to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid deliver device 100. The fluid delivery device 100 may also include a housing 104 to enclose the circuit board 101, the chassis 102, and the components 110, 130, 150, 170, 180.

The fluid delivery device 100 may also include integrated monitoring such as continuous glucose monitoring (CGM). A monitor test strip 120 coupled to a monitor (not shown) in the device 100 may be introduced by the transcutaneous access tool 172 subcutaneously. One example of the monitor test strip is a CGM test strip (such as the type available from Nova Biomedical) which may be understood as a glucose sensor configured to test for a concentration level of glucose in the blood of a patient. The fluid delivery device 100 may be configured to receive data from the monitoring test strip concerning a glucose level of the patient, and determining an output of insulin from the reservoir based on the glucose level.

The transcutaneous access tool 172 includes an introducer trocar or needle 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172.

Figure 6:
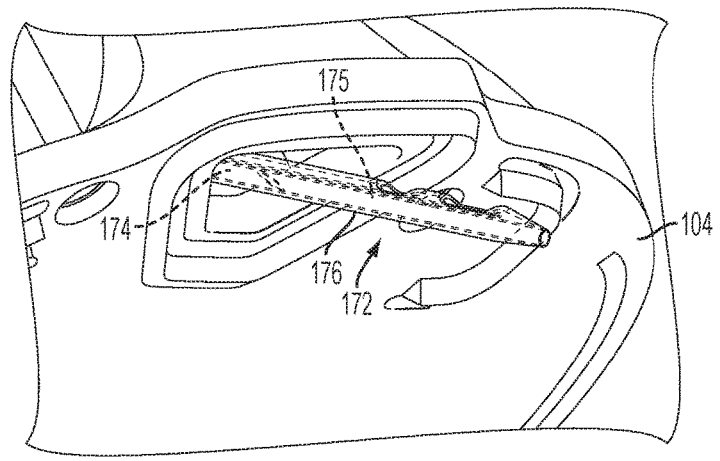
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

Referring to FIGS. 7-12, one embodiment of the fluid drive mechanism 150 uses a clutch mechanism 160 to facilitate filling of the reservoir 130 and engagement of the fluid drive mechanism 150 for driving fluid out of the reservoir 130. The fluid drive mechanism 150 includes a first threaded member in the form of an elongated shaft such as a threaded drive rod or leadscrew 152, with external threads extending from a plunger 136 received in the reservoir 130 and sealed with an o-ring 137 against the inside surface of the reservoir 130. The leadscrew 152 and plunger 136 may be an inseparable, insert-molded assembly. A second threaded member in the form of an elongated shaft such as a tube nut 154 with internal threads threadably engages the leadscrew 152 and may be driven by a drive wheel 156 via a clutch mechanism 160.

When the reservoir 130 is empty (FIGS. 7 and 8), the plunger 136 is positioned at one end of the reservoir 130 such that the plunger 136 is extended and the clutch mechanism 160 is disengaged. In certain embodiments, the reservoir 130 may be filled with fluid, particularly insulin, by opening an inlet port to the reservoir 130 and pumping in the insulin under sufficient hydraulic pressure to retract the plunger 136 within the reservoir 130. Thereafter, the inlet port may be closed. When the reservoir 130 is filled and the plunger 136 moves to the opposite (retracted) end of the reservoir 130 (FIG. 9), the clutch mechanism 160 remains disengaged to allow the tube nut 154 to pass into an elongated cylindrical bore (along the drive axis) of a hub of the drive wheel 156. The clutch mechanism 160 may then be engaged (FIGS. 10-12) such that rotation of the drive wheel 156 causes the clutch mechanism 160 to rotate the tube nut 154, which causes the leadscrew 152 to advance the plunger into the reservoir 130 to deliver the fluid from the reservoir 130. In alternative embodiments, the reservoir 130 may be filled when the plunger 136 is already retracted.

Figure 7:
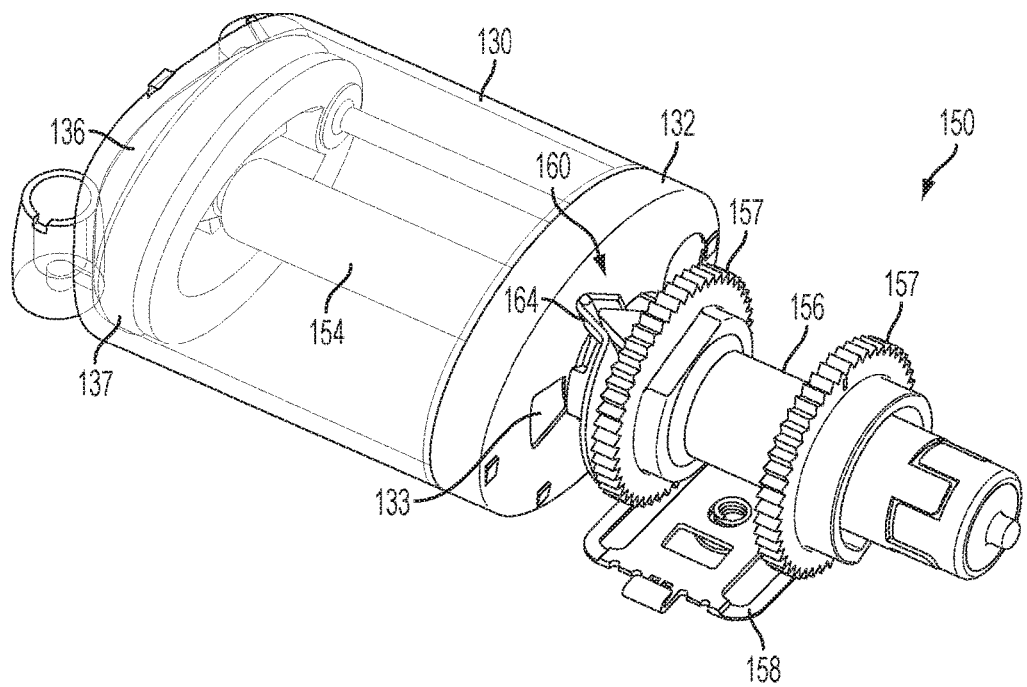
FIG. 7 is a top perspective view of a fluid driving mechanism of the fluid delivery device shown in FIG. 1 with a clutch mechanism in a disengaged position prior to filling.
Figure 8:
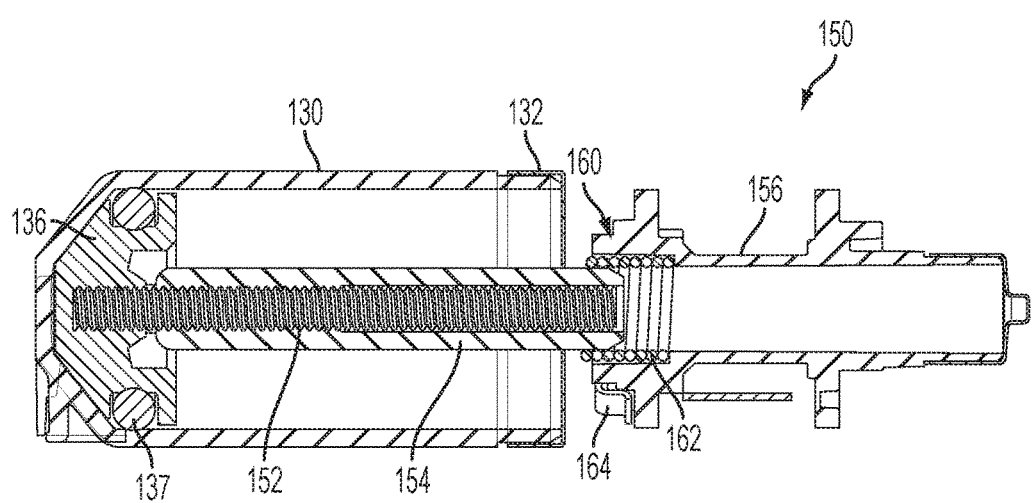
FIG. 8 is a side cross-sectional view of the fluid driving mechanism shown in FIG. 7.
Figure 9:
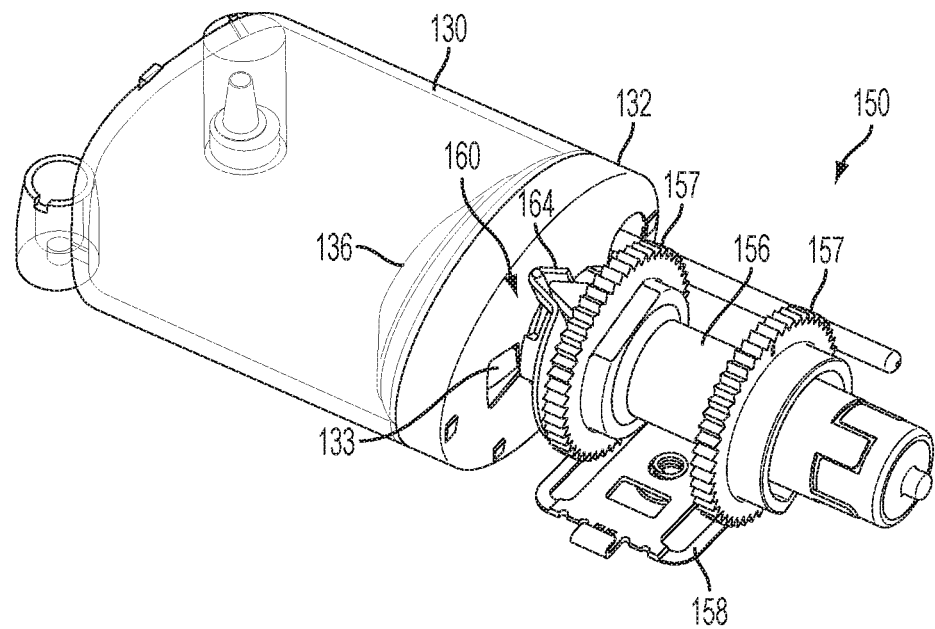
FIG. 9 is a top perspective view of the fluid driving mechanism shown in FIG. 7 with the clutch mechanism in a disengaged position after filling.
Figure 10:
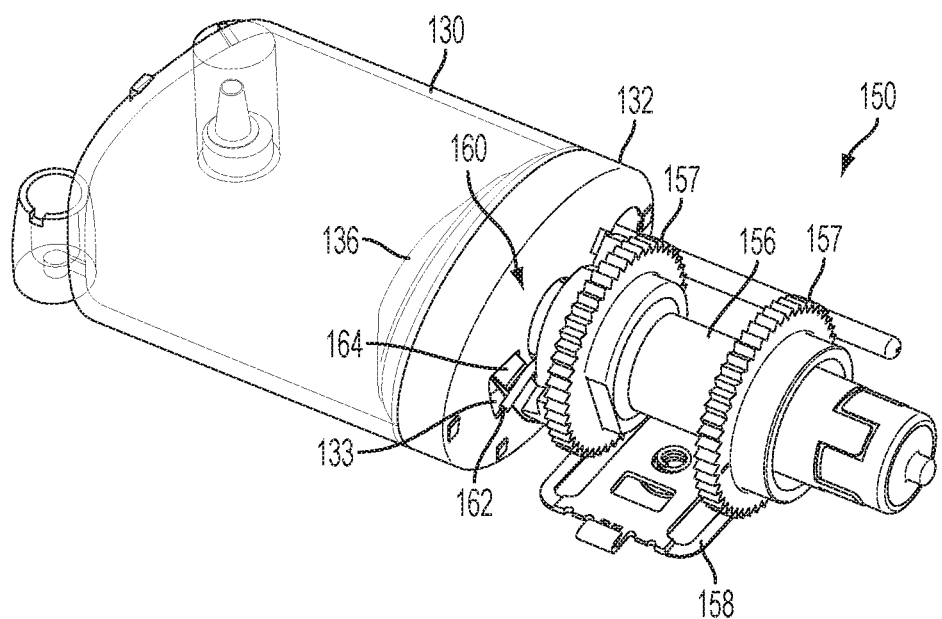
FIG. 10 is a top perspective view of the fluid driving mechanism shown in FIG. 7 with the clutch mechanism being released to the engaged position.
Figure 11:
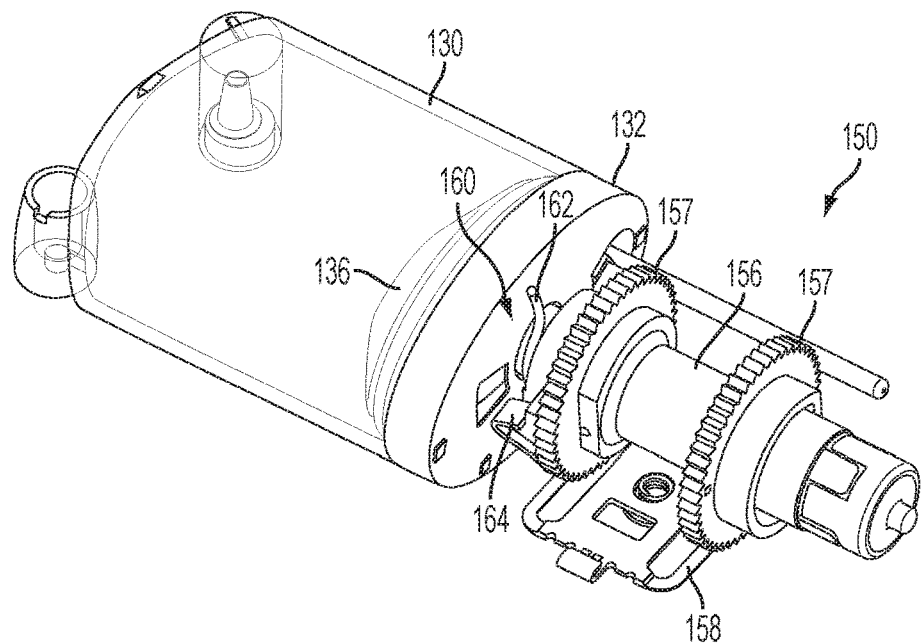
FIGS. 11 and 12 are top perspective views of the fluid driving mechanism shown in FIG. 7 with the clutch mechanism in the engaged position.
Figure 12:
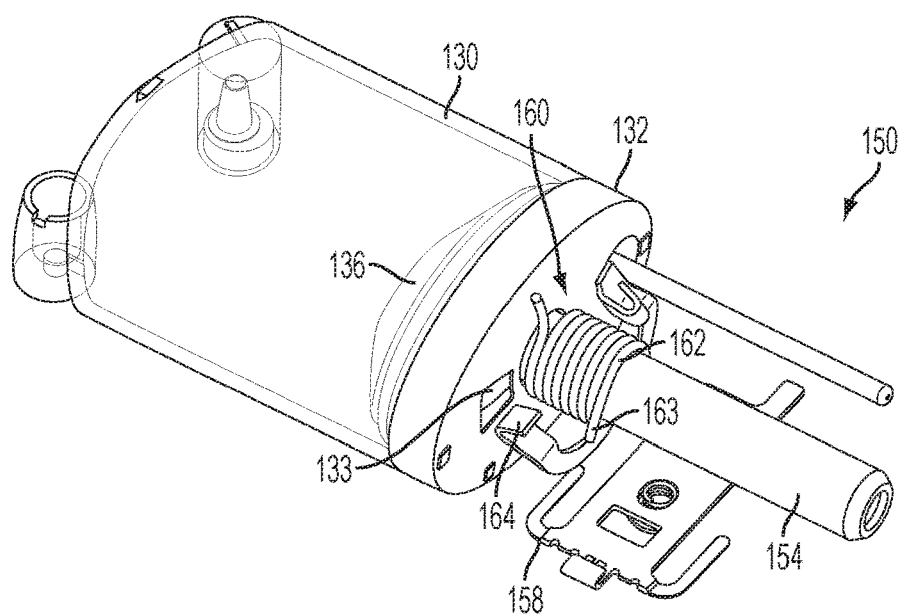

In the illustrated embodiment, the clutch mechanism 160 includes a clutch spring 162 (e.g., a helical torsion spring) located in a counterbore at one end of the drive wheel 156, adjacent the reservoir 130. The inside diameter of the clutch spring 162 is larger than the outside diameter of the tube nut 154 when the clutch spring 162 is loaded, thereby disengaging the clutch spring 162 from the tube nut 154 and allowing the tube nut 154 to pass through the center aperture of the spring 162 and into the elongated bore of the drive wheel 156. Alternatively, the inside diameter of the clutch spring 162 is smaller than the outside diameter of the tube nut 154 when the clutch spring 162 is unloaded, thereby engaging or gripping the tube nut 154 and allowing the drive wheel 156 to rotate the tube nut 154. In the illustrated embodiment, prior to filing the reservoir 130, the clutch spring 162 is held in the loaded, disengaged position by a spring latch 164 engaged with the drive wheel 156 (FIGS. 7-9). After the reservoir 130 has been filled, the clutch spring 162 may thus be engaged by rotating the drive wheel 156 until the spring latch 164 releases the clutch spring 162 (FIG. 10) allowing the clutch spring 162 to unload and grip the tube nut 154 (FIGS. 11 and 12), at which time fluid may be dispensed from the reservoir 130 with continued rotation of the drive wheel 156.

As shown, the spring latch 164 may be biased by the clutch spring 162 such that as the drive wheel 156 rotates the spring latch 164 moves rotationally against a surface of a reservoir cap 132 until clutch spring 162 deflects the spring latch 164 into a window 133 in the reservoir cap 132. When the spring latch 164 moves into the window 133, the end of the clutch spring 162 held by the spring latch 164 is released, thus engaging the clutch mechanism 160. When the clutch spring 162 is engaged, the drive wheel 156 contacts an end 163 of the clutch spring 162 to create a thrust on the clutch spring 162 that causes the clutch spring 162 to rotate the tube nut 154. The fluid drive mechanism 150 may also use other clutch mechanisms capable of allowing the tube nut 154 or other type of nut or threaded member to pass through the clutch mechanism and then being activated to engage the nut or threaded member.

In the illustrated embodiment, the drive wheel 156 includes ratchets 157 that are engaged by an actuator 158 to incrementally drive the wheel 156 and advance the plunger 136 into the reservoir 130. Examples of this actuation mechanism are described in greater detail in U.S. Patent Application Publication No. 2005/0238507, which is fully incorporated herein by reference.

By using a clutch mechanism, the engagement between the leadscrew and the nut occurs at assembly, and thus no rotation is needed for the nut to engage the leadscrew by operation of the device. This reduces the number of fluid path prime pulses to prime the pump and assures a full and proper priming of the fluid path before placement on the body. The clutch mechanism also enables the changing of thread pitch for other drug applications without a need to redesign the tilt nut used in fluid driving mechanisms in other existing pumps. The components of the clutch mechanism are also more easily inspected than the tilt nut assembly.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A fluid delivery device comprising: a fluid reservoir; a transcutaneous access tool fluidly coupled to the fluid reservoir; and a drive mechanism for driving fluid from the fluid reservoir, the drive mechanism comprising: a plunger received in the fluid reservoir; an elongated assembly comprising a first elongated member and a second elongated member; the first elongated member extending from the plunger; the second elongated member coupled to the first elongated member; a drive wheel; and a clutch mechanism coupled to the drive wheel wherein the clutch mechanism is configured to allow the second elongated member to pass through when disengaged and is configured to grip the second elongated member without threaded engagement when engaged, such that the drive wheel rotates the second elongated member to advance the first elongated member and the plunger into the fluid reservoir.

2. The fluid delivery device of claim 1 wherein: the first elongated member comprises a first threaded member; the second elongated member comprises a second threaded member; the second threaded member is in threaded engagement with the first threaded member, and the clutch mechanism is configured to allow the second threaded member to pass through when disengaged and is configured to grip the second threaded member without threaded engagement when engaged, such that the drive wheel rotates the second threaded member to advance the first threaded member and the plunger into the fluid reservoir.

3. The fluid delivery device of claim 2 wherein the first elongated threaded member comprises a first threaded shaft having external threads.

4. The fluid delivery device of claim 2 wherein the second elongated threaded member comprises a second threaded shaft having internal threads.

5. The fluid delivery device of claim 1 wherein the clutch mechanism includes a clutch spring that grips the second elongated member without threaded engagement when released.

6. The fluid delivery device of claim 5 wherein the clutch mechanism further includes a spring latch configured to hold the clutch spring in a disengaged position and configured to release the clutch spring such that the clutch spring moves to an engaged position.

7. The fluid delivery device of claim 6 wherein the spring latch is configured to release the clutch spring in response to movement of the drive wheel.

8. A method of operating a fluid delivery device comprising: providing the fluid delivery device, the device comprising a fluid reservoir; a transcutaneous access tool fluidly coupled to the fluid reservoir; and a drive mechanism for driving fluid from the fluid reservoir, the drive mechanism comprising an elongated assembly comprising a first elongated member and a second elongated member; the first elongated member extending from a plunger; the second elongated member coupled to the first elongated member; a drive wheel; and a clutch mechanism coupled to the drive wheel, wherein the clutch mechanism is configured to allow the second elongated member to pass through when disengaged and is configured to grip the second elongated member to pass through when disengaged and is configured to grip the second elongated member without threaded engagement when engaged, such that the drive wheel rotates the second elongated member to advance the first elongated member and the plunger into the fluid reservoir; holding the clutch mechanism in a disengaged position; filing the fluid reservoir with fluid; passing the second elongated member through the clutch mechanism such that the plunger is retracted within the fluid reservoir; releasing the clutch mechanism from the disengaged position; and engaging the clutch mechanism with the second elongated member.

9. The method of claim 8 wherein: the first elongated member comprises a first threaded member; the second elongated member comprises a second threaded member; the second threaded member is in threaded engagement with the first threaded member; and the clutch mechanism is configured to allow the second threaded member to pass through when disengaged and is configured to grip the second threaded member without threaded engagement when engaged, such that the drive wheel rotates the second threaded member to advance the first threaded member and the plunger into the fluid reservoir.

10. The method of claim 8 wherein:
the clutch mechanism includes a clutch spring; and
passing the second elongated member through the clutch mechanism further comprises passing the second elongated member through the clutch spring of the clutch mechanism.

11. The method of claim 10 wherein:
engaging the clutch mechanism with the second elongated member further comprises gripping the second elongated member without threaded engagement with the clutch spring.

12. The method of claim 10 wherein:
the clutch mechanism includes a spring latch; and
holding the clutch mechanism in a disengaged position further comprises holding the clutch spring in a disengaged position with the spring latch.

13. The method of claim 12 wherein:
releasing the clutch mechanism from the disengaged position further comprises releasing the clutch spring from the spring latch.

14. The method of claim 13 further comprising:
rotating the drive wheel to release the clutch spring from the spring latch.

15. The method of claim 8 further comprising: rotating the drive wheel to dispense e fluid from the fluid reservoir.

* * * * *